(12) United States Patent
Rekow et al.

(10) Patent No.: US 11,474,096 B2
(45) Date of Patent: Oct. 18, 2022

(54) BREATH ALCOHOL MEASUREMENT WITH CONTACTLESS SAMPLE COLLECTION

(71) Applicant: Dräger Safety AG & Co. KGaA, Lübeck (DE)

(72) Inventors: Jens Rekow, Lübeck (DE); Stefan Morley, Lübeck (DE); Stefan Barten, Lübeck (DE); Carsten Stemich, Ratzeburg (DE); Michael Richenberger, Scharbeutz (DE); Sebastian Schröter, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 414 days.

(21) Appl. No.: 16/641,558

(22) PCT Filed: Aug. 14, 2018

(86) PCT No.: PCT/EP2018/072002
§ 371 (c)(1),
(2) Date: Feb. 24, 2020

(87) PCT Pub. No.: WO2019/038131
PCT Pub. Date: Feb. 28, 2019

(65) Prior Publication Data
US 2020/0173981 A1 Jun. 4, 2020

(30) Foreign Application Priority Data
Aug. 25, 2017 (DE) .................... 10 2017 008 008.9

(51) Int. Cl.
*G01N 33/497* (2006.01)
*A61B 5/097* (2006.01)
*A61B 5/08* (2006.01)

(52) U.S. Cl.
CPC ......... *G01N 33/4972* (2013.01); *A61B 5/097* (2013.01); *A61B 5/082* (2013.01)

(58) Field of Classification Search
CPC ...... G01N 33/4972; A61B 5/097; A61B 5/082
See application file for complete search history.

(56) References Cited

U.S. PATENT DOCUMENTS

| 4,852,583 A | 8/1989 | Walker |
| 2011/0098590 A1 | 4/2011 | Garbutt |

(Continued)

FOREIGN PATENT DOCUMENTS

| CN | 102316801 A | 1/2012 |
| DE | 8225425 U1 | 7/1985 |

(Continued)

*Primary Examiner* — Jennifer Wecker
*Assistant Examiner* — Oyeleye Alexander Alabi
(74) *Attorney, Agent, or Firm* — McGlew and Tuttle, P.C.

(57) ABSTRACT

A breath alcohol measurement device has a sample collector (1) with a sample inlet (2) configured for a contactless introduction of a breath sample. A measurement unit (9) has a sensor (16) that generates a measurement signal based on an alcohol content in the breath sample. A control and evaluation unit (4) determines the alcohol content based on the measurement signal and transmits a result-specific signal to an output unit (5). Some of the breath sample provided into the sample inlet (2) is applied, at least intermittently via a main flow duct (10), to the sensor (16) via a measurement gas duct (21) that is connected via an outlet to the environment (7). Between the sample inlet (2) and the outlet of the main flow duct there is a further outflow opening (6) through which some of the breath sample introduced into the sample inlet exits into the environment.

18 Claims, 4 Drawing Sheets

(56) References Cited

U.S. PATENT DOCUMENTS

| | | |
|---|---|---|
| 2011/0283770 A1* | 11/2011 | Hok ........................ A61B 5/097 73/23.3 |
| 2011/0283771 A1 | 11/2011 | Hok |
| 2013/0231871 A1 | 9/2013 | Hok |
| 2013/0281873 A1 | 10/2013 | Evans et al. |

FOREIGN PATENT DOCUMENTS

| | | |
|---|---|---|
| EA | 025809 B1 | 12/2014 |
| JP | 4740263 B2 | 8/2011 |
| JP | 4997350 B1 | 8/2012 |
| JP | 2013156169 A | 8/2013 |
| WO | 2007083350 A1 | 7/2007 |
| WO | 2012064252 A1 | 5/2012 |
| WO | 2014031071 A1 | 2/2014 |
| WO | 2017062017 A1 | 4/2017 |

* cited by examiner ered out of the
breath alcohol measuring device on a side located opposite
the sample inlet.

Funnel-shaped sample inlets, into which the test subject
has to discharge the sample, are usually used in case of
contactless measurements of the breath alcohol content. It is
often problematic in case of the prior-art sample inlets that
comparatively high dynamic pressures are initiated in certain areas of the funnel and uncontrolled backflows may
occur in some cases. This can be attributed, in particular, to
the fact that the prior-art devices have a closed funnel with
a large inlet opening and with a tapered cross section. Such
backflows out of the funnel often reach the face of the person
carrying out the measurement or lead to swirlings in front of
the face, which is regularly perceived as disturbing or
unhygienic by the test subjects.

In addition, an overpressure in the funnel which leads to
the flushing of the funnel being insufficient forms due to
such a closed construction of the funnel during the flowing
in of the gas. This, in turn, then leads in many cases to the
sensor not being sufficiently acted on by breathing gas and
the correct measurement of the concentration of the breath
alcohol being compromised.

BREATH ALCOHOL MEASUREMENT WITH CONTACTLESS SAMPLE COLLECTION

CROSS REFERENCE TO RELATED APPLICATIONS

This application is a United States National Phase Application of International Application PCT/EP2018/072002, filed Aug. 14, 2018, and claims the benefit of priority under 35 U.S.C. § 119 of German Application 10 2017 008 008.9, filed Aug. 25, 2017, the entire contents of which are incorporated herein by reference.

TECHNICAL FIELD

The present invention pertains to a device for the measurement of breath alcohol with a sample collector, into which a breath sample is introduced by a test subject via a sample inlet, without there being any contact between the mouth of the test subject and the sample inlet. The breath alcohol measuring device has a sensor unit, to which the breath sample flowing out at least partly through the collector outlet of the sample collector can be fed and which generates a measured signal on the basis of the alcohol content contained in the breath sample. Further, a control and analysis unit is provided, which determines the alcohol content of the breath sample on the basis of the measured signal and sends a result-specific signal to an output unit, which provides information about the breath alcohol content of the breath sample.

TECHNICAL BACKGROUND

The breath alcohol measuring devices that are usually used have mouthpieces, which have to be put into the mouth by the test subject during sample collection. The mouthpieces are changed between the individual samples or replaceable covers are placed onto a mouthpiece to prevent contact of the mouthpiece by different test subjects.

Before the actual testing of the breath sample, the breath alcohol measuring device monitors whether the mouthpiece was blown into and then determines the breath volume introduced into the device. It is ensured by this procedure that only unmixed or undiluted breathing air is used for the measurement. The breath alcohol measuring device then removes from this breathing air stream by means of suitable devices a partial volume that is fed to the actual sensor, which is often configured as an electrochemical sensor.

It is, however, appropriate in many applications that a rapid sequence of measurements be carried out with different test subjects. A change of the mouthpieces is not desired in this case for reasons of cost and time. In order to carry out such measurements, for example, to allow the test subject access to a certain safety area, the test subject blows in the direction of an inlet opening of the sample collector of a breath alcohol measuring device, without there being contact between the sample collector and the mouth of the test subject.

Such a breath alcohol measuring device, which makes possible a contactless sample collection, is described, for example, in WO 2014/031071 A1. The breath alcohol measuring device has a sample collector with a sample inlet opening, into which the test subject discharges his breath sample by blowing in. Elements are provided within the breath alcohol measuring device in order to retain the collected sample at least temporarily and to supply a sensor with breathing air of the test subject. Excessive air or air already used for a measurement is again guided out of the breath alcohol measuring device on a side located opposite the sample inlet.

SUMMARY

Based on the prior-art breath alcohol measuring devices, in which the collection of breath samples is carried out without contact with a mouthpiece, and the problems explained above, a basic object of the present invention is to provide such a device of the type of this class, in which a reliable flow through the sample inlet is guaranteed. Backflows within the sample collector shall be avoided in a reliable manner, especially also independently of the intensity and the angle of incidence at which the breathing air stream enters the sample inlet and the sample collector. The sample collector being used shall, furthermore, be robust, easy to clean and comparatively simple to manufacture. The sample collector being indicated shall, furthermore, make it possible to be able to be fastened to the measuring device in a replaceable manner, so that this sample collector can be replaced as needed at specific time intervals.

The present invention pertains to a device for breath alcohol measurement with a sample collector, into which a breath sample can be introduced by the test subject via a sample inlet, without there being contact between the test subject and the sample inlet.

The device has for this purpose a funnel-shaped sample collector, into which a breath sample can be introduced by the test subject via a sample inlet, and a sensor arranged in a measuring unit, to which at least a part of the breath sample discharged into the sample inlet can be fed and which generates a measured signal on the basis of the alcohol content contained in the breath sample. Furthermore, a control and analysis unit is provided, which determines the alcohol content of the breath sample on the basis of the measured signal and sends a result-specific signal to an output unit, which provides information about the breath alcohol content of the breath sample. The device for measuring the breath alcohol content according to the present invention has been perfected by a main flow duct extending in the interior of the sample collector adjoining the sample inlet, from which main flow duct a part of the breath sample discharged into the sample inlet acts at least at times on the sensor via a measured gas duct and which opens into a surrounding area in the direction of flow behind the measured gas duct via an outlet, and by at least one additional outflow opening being provided between the sample inlet and the outlet of the main flow duct, through which outflow opening a part of the breath sample introduced into the sample inlet is released into a surrounding area before reaching the outlet of the main flow duct. It is, in principle, conceivable that this additional outflow opening is selectively arranged in front of, behind or in an area of the main flow duct, in which the measured gas duct leading to the sensor branches off from the main flow duct.

The device according to the present invention is thus characterized in that at least one additional outflow opening, through which a part of the breath sample being discharged by the test subject is released, is provided between the sample inlet and the outlet, preferably between the sample inlet and a collector outlet of the sample collector. A suitable flow through the main flow duct, especially through the sample collector, which has a funnel-shaped configuration, is ensured by this technical feature. Especially the formation of very high dynamic pressures in individual areas of the sample collector and, in addition, backflows are hereby avoided in a reliable manner. The provision of corresponding outflow openings represents a technical feature that can be embodied in a comparatively simple manner, which brings about an extremely surprising technical effect.

In a special embodiment, the sample collector is connected to a measuring unit, in which the main flow duct extends and the sensor is arranged, and has a collector outlet, via which the breath sample discharged into the sample collector is introduced into a part of the main flow duct that is located in the measuring unit. According to this preferred embodiment, the at least one outflow opening is arranged between the sample inlet and the collector outlet.

Further, it is advantageously conceivable that the sample collector has a funnel-shaped or conical configuration. With such a sample collector, which has especially a funnel-shaped configuration, a comparatively large volume of breathing gas is fed in an at least almost undiluted form with ambient air to the sensor, which is arranged in the measuring unit, which is arranged downstream in relation to the flow. For this purpose, the breathing gas introduced from the sample collector into the part of the main flow duct extending in the measuring unit of the breath alcohol measuring device is preferably continuously guided past a branch or past a suction opening and a part of the breathing gas stream flowing past is suctioned into the measured gas duct leading to the sensor for the measurement. It is ensured by this technical feature that at a suitable time a measured volume can be removed from the volume flow flowing past from the main flow duct via the branch, which is representative of the so-called deep lung air.

Provisions are made in a special embodiment of the present invention for the sample collector to have at least one fastening element, by means of which the sample collector can be connected to the measuring unit of the breath alcohol measuring device, in which the sensor is arranged. The main flow duct also extends in this case starting from the sample collector in the measuring unit, where a measured gas duct in the area of a branch leads to the sensor. It is ensured due to the provision of such a fastening element that the sample collector configured according to the present invention can be replaceably fastened to the measuring unit of an alcohol measuring device in a simple manner. Based on this feature, it is possible in a comparatively simple manner to change a preferably funnel-shaped sample collector as needed, especially at defined time intervals. The replacement preferably takes place in a non-destructive manner and without using tools. It is conceivable, as an alternative, to configure the fastening elements and/or the sample collector such that once it has been removed from the measuring unit of a breath alcohol measuring device, this sample collector cannot again be fastened to this measuring unit. This can be ensured, for example, by means of safety elements which break off or are destroyed in a different manner once the sample collector has been removed from the measuring unit, so that a refastening of the sample collector to the measuring unit is ruled out.

It is conceivable according to a variant that the at least one additional outflow opening is shaped and dimensioned such that after introduction of the breath sample into the sample collector, a pressure that is different than the pressure in the surrounding area is generated at the sensor for the detection of the breath alcohol content and/or at a pressure sensor, via which the supply of the sensor for the detection of the breath alcohol content is controlled. It is essential for the at least one additional outflow opening that a good flow through the preferably funnel-shaped sample collector is guaranteed, on the one hand, and, on the other hand, a continuous breathing air stream is generated, which makes possible a satisfactory supply of the sensor for the detection of the breath alcohol content.

It is generally conceivable that the sensor for the detection of the breath alcohol content is arranged in a flow duct, which is configured such that the sample is introduced into this flow duct and is discharged again in the opposite direction, without additional auxiliary devices being provided. A pump unit may likewise be provided, which is actuated, for example, via a pressure sensor, and which feeds the sample to the sensor as a partial flow of a total volume flow guided past or arising at a branch. In this case, the amount of breathing air needed to carry out the test advantageously branches off from the main flow duct into the measured gas duct of the measured air branch when reaching or exceeding a pressure limit value at the pressure sensor. Provided that the necessary sample volume is suctioned into the measured gas duct by means of a pumping unit, this offers the advantage that a reproducible measurement and analysis of the breath sample is always carried out.

Furthermore, it is advantageous when the at least one additional outflow opening is shaped and dimensioned such that the generation of a measured signal by the sensor based on environmental effects that are not caused by the discharge of the breath sample is prevented. Especially when a breath alcohol measuring device is used outdoors, both the moisture content and the temperature of the surrounding area may vary considerably in some cases. This variation of the ambient conditions should be negligible for the analysis of the breath alcohol sample of the test subject. Hence, at least one heating element, which reliably prevents condensation phenomena within the breath alcohol measuring device, especially within the measuring unit, is preferably provided in the area of the sample collector and/or in the direction of flow behind the collector outlet of the sample collector.

In another embodiment, the sample collector has at least one retaining element, which protrudes inwards into the main flow duct and which at least partly prevents a backflow of the breath sample discharged into the sample inlet in the direction of the sample inlet. Such a retaining element may be configured, for example, in the form of a collar enclosing the sample inlet circumferentially. It is also conceivable to provide individual elements in the interior of the sample collector, especially in the area of the sample inlet, which elements protrude into the interior space and represent flow obstacles for air streams, which are directed in the direction of the sample inlet.

According to another special configuration of the present invention, the retaining element has at least one fastening element, which is configured such that the retaining element can be connected to the sample collector in a non-destructive manner and can be detached again in a non-destructive manner after the connection. Advantageously, it is further conceivable that the retaining element is configured with the sample inlet as a one-part component, which can be changeably fastened to the sample collector. It is likewise conceivable that the retaining element is configured as a separate component, which is connected as needed in a simple manner to the sample collector, especially by means of a plug-in connection and/or snap-in connection. Depending on the selected embodiment, it is thus possible in a simple manner to replace the retaining element with or without the sample inlet, as needed.

The at least one additional outflow opening advantageously has at least two slots made in an outer wall of the sample collector. The slots are configured here such that a part of the breathing gas stream introduced by the test subject into the sample inlet of the sample collector flows out of the sample collector into the surrounding area, and thus there is a uniform flow through the sample collector towards the collector outlet. The outflow opening is preferably formed by a plurality of openings, which are made in an outer wall of the sample collector distributed over the circumference of the flow duct.

Furthermore, it is conceivable that a cross section of the main flow duct is reduced from the sample inlet to the sample outlet in the sample collector. It is, in principle, conceivable that such a reduction of the flow cross section takes place continuously or in individual discrete steps. It is especially advantageous when the main flow duct of the sample collector has a trapezoidal cross-sectional shape in at least one plane in the area of the collector outlet. It is useful in this case when the counterpiece of the measuring unit of the breath alcohol measuring device, which is connected to the collector outlet, especially to the collector outlet having a trapezoid shape, has at least one similar cross section. In addition or as an alternative, it is further conceivable that an at least partial deflection of the breathing gas stream takes place in the area of the collector outlet. It is conceivable in this connection, for example, that the breathing gas stream flows into the measuring unit. The main flow duct according to this embodiment is thus split into two partial flow ducts at least temporarily in the area of the collector outlet, which partial flow ducts merge again into the one main flow duct in connection with the collector outlet. Due to the specific deflection and/or splitting of the breathing gas stream in the area of the collector outlet, it is, in turn, possible to ensure especially advantageous flow conditions in the sample collector and in the measuring unit, especially an especially suitable flow through the main flow duct as well as supply of measured gas to the sensor, due to suitable dimensioning of the corresponding flow resistances.

In a special variant of the present invention, the sample collector has at least one fastening element, so that the sample collector can be connected in a non-destructive manner and without tools to the measuring unit, in which the sensor is arranged, and can be detached again in a non-destructive manner after the connection.

Furthermore, it is conceivable that at least one flow-influencing component, especially a screen, a diaphragm, a flap and/or a valve is provided between the sample inlet of the sample collector and the sensor in the area of the main flow duct.

In addition to a breath alcohol measuring device with a suitably configured sample collector, the present invention pertains, moreover, to a sample collector that has the special properties described above and that can preferably be connected to a breath alcohol measuring device, especially to a measuring unit of a breath alcohol device, in which are located a sensor for carrying out the measurement of a breath alcohol content, a power supply, a display and a control and analysis unit. It is essential for the sample collector according to the present invention that this sample collector makes possible a reliable, uniform flow through the sample collector, on the one hand, and thus provision of a proper measured gas stream for the sensor is guaranteed, on the other hand. Locally extremely elevated dynamic pressures, swirlings and/or backflows within the sample collector are especially prevented in a comparatively simple manner due to the configuration according to the present invention. In addition, it is conceivable that the sample collector has in at least some areas a suitable coating, which is hygienically effective and/or influences the flow properties of the breathing air stream flowing through the sample collector.

The present invention will be explained in more detail below without limitation of the general idea of the invention on the basis of exemplary embodiments with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
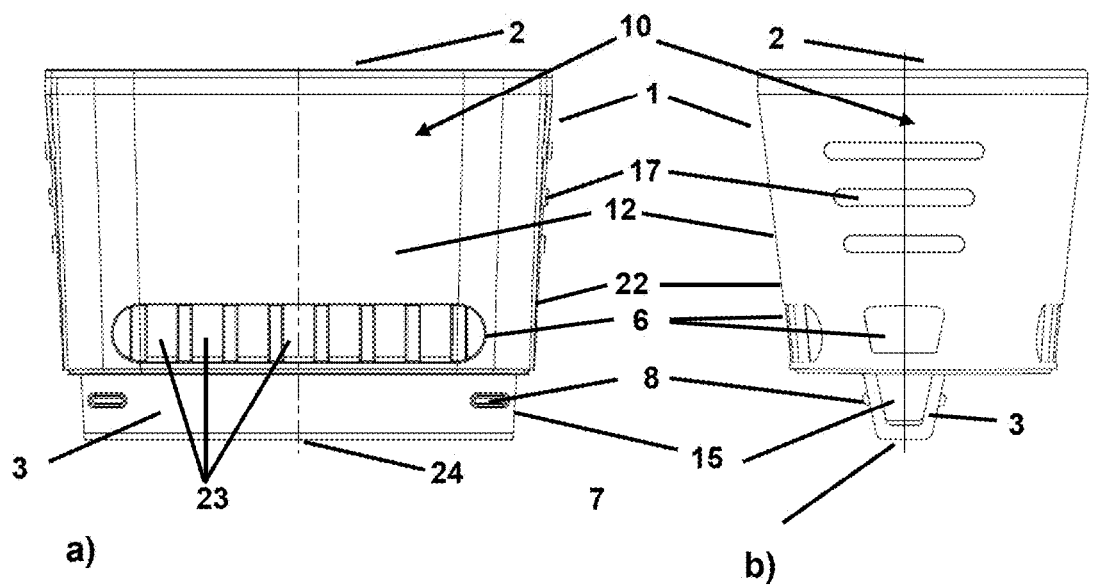
FIG. 1 is a front view and a side view of a sample collector for a breath alcohol measuring device configured according to the present invention, which makes possible a contactless collection of a breath sample for a test subject.
Figure 4:
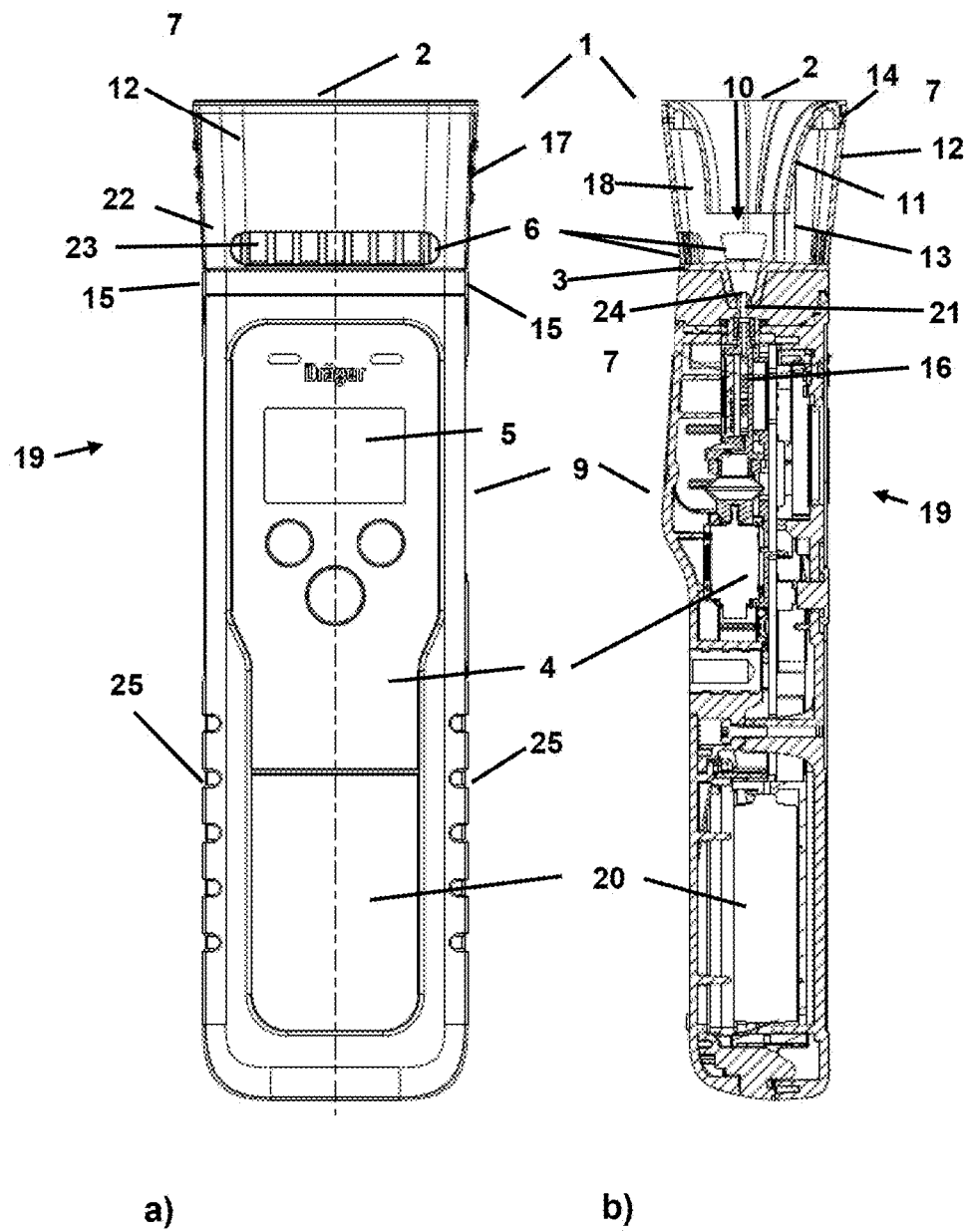
FIG. 4 is a front view and a sectional view showing the breath alcohol measuring device with the sample collector as well.

Referring to the drawings, FIG. 1 shows in a front view according to FIG. 1*a* and in a side view according to FIG. 1*b* a sample collector 1 configured according to the present invention for a breath alcohol measuring device 19 configured according to the present invention. The breath alcohol measuring device 19, which has a measuring unit 9 and a sample collector 1 fastened to it, is shown in FIG. 4. The sample collector 1 shown in two views has a sample inlet 2, into which a test subject discharges a breath sample, without the sample inlet 2 or the sample collector 1 having to be touched for this purpose. Rather, the breath sample is blown into the sample inlet 2 during the sample collection, without there being contact with the sample inlet 2. The sample collector 1 has a funnel-shaped configuration, so that the breath sample discharged by the test subject is directed into a main flow duct 10 arranged in the interior of the sample collector 1. Through this main flow duct 10, the breath sample reaches the collector outlet 3 of the sample collector 1 from the sample inlet 2.

A special fastening element 8, which makes possible a fastening of the sample collector 1 to the measuring unit 9 of the breath alcohol measuring device 19, is provided in the area of the collector outlet 3. Especially the sensor 16 for the detection of the breath alcohol content, a control and analysis unit 4, a power supply 20, which has preferably at least one chargeable battery, as well as an output unit 5, especially in the form of a display, are located in the measuring unit 9. The fastening element 8 in the area of the collector outlet 3 is configured such that the sample collector 1 can be fastened to the measuring unit 9 of the breath alcohol measuring device 19 and can again be detached from same in a non-destructive manner and without the aid of a tool. The main flow duct 10 within the measuring unit 9 extends downstream of the collector outlet 3, wherein the breathing gas stream discharged by the test subject is continuously guided in at least some cases over a measured gas duct 21 to the sensor 16, so that the sensor 16 is supplied with a necessary sample volume as needed.

Figure 6:
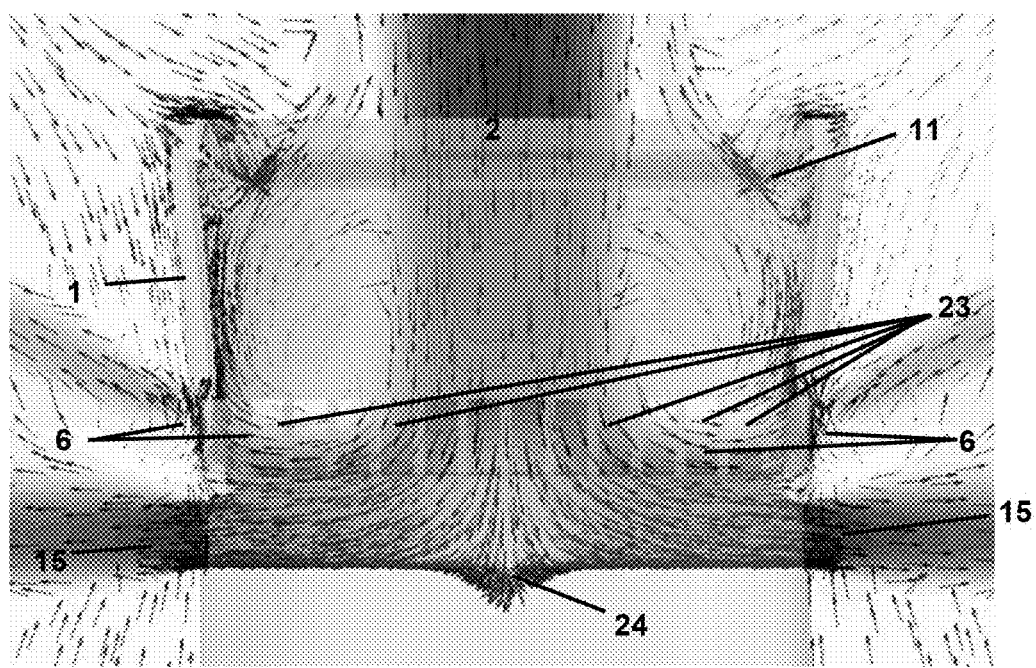
FIG. 6 is a view showing flow graphics of a sample collector with flow openings provided according to the present invention.

It is essential to the present invention for the sample collector 1 shown in FIG. 1 that an additional outflow opening 6, which has a plurality of slots or openings 23 arranged next to one another, be provided in the lower area. Due to the outflow openings 6 with the corresponding slots 23 provided in this area, at least a part of the breath sample blown into the sample inlet 2 reaches a surrounding area 7 of the sample collector 1. This part of the breath sample, which reaches the surrounding area 7 through the outflow opening 6, is not fed to the measuring unit 9 with the sensor 16, but rather it reaches the surrounding area 7 before the remaining part of the breath sample flows into the collector outlet 3. Because of the provision of outflow openings 6 in the form of slots 23, an especially suitable flow through the main flow duct 10 in the interior of the sample collector 1 is made possible. Especially locally elevated dynamic pressures as well as backflows in the direction toward the sample inlet 2 through the outflow openings 6 provided are prevented in a reliable manner. In addition, FIG. 6 shows for this the flow pattern of a sample collector 1, through which a breath sample flows. This flow pattern will be explained in more detail later.

In the exemplary embodiment shown in FIG. 1, the collector outlet 3 has a total of three outlets, via which the breathing gas stream discharged by the test subject into the sample inlet 2 of the sample collector 1 flows out of the collector outlet 3. The main flow duct 10 ends at the two outlets 15 arranged on the side or opens into the surrounding area 7. A part of the breathing gas stream discharged by the test subject reaches the measured gas duct 21 of the measuring unit 9 and finally the sensor 16 for breath alcohol determination via an opening 24 located on the bottom side of the collector outlet 3 and in alignment with the sample inlet 2. After the measurement has been completed, the breathing gas located in the measured gas duct 21 flows back into the collector outlet 3 and finally into the surrounding area 7 via the lateral outlet openings 24.

As an alternative, it is conceivable that the measured gas duct is vented via a different opening, especially via an outlet provided in the measuring unit 9.

Figure 2:
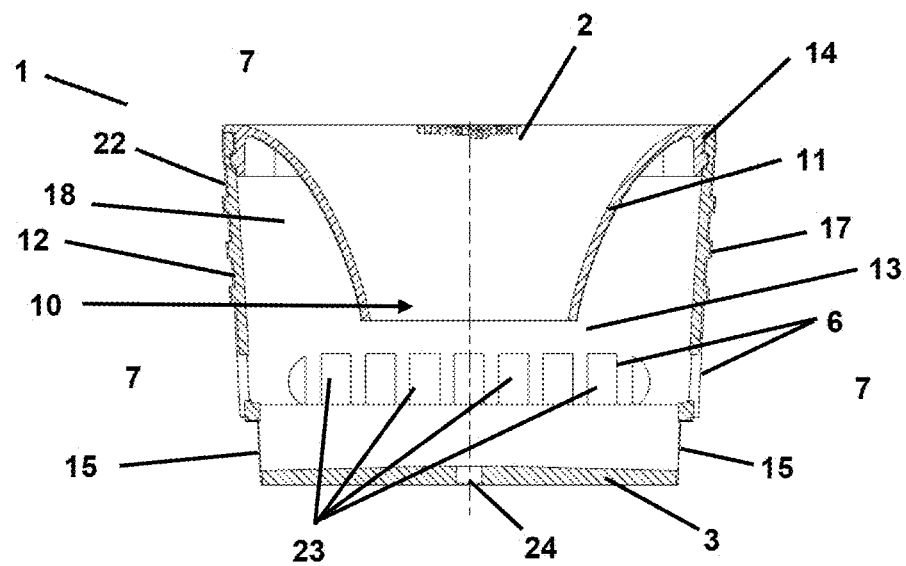
FIG. 2 is a sectional view of a sample collector configured according to the present invention.

FIG. 2 shows the sample collector 1 configured according to the present invention in a sectional view. The sample collector 1 has a funnel-shaped configuration and has an outer wall 12, at which are provided outwardly directed projections 17, which make possible an easy grasping and fastening of the sample collector 1 at a measuring unit 9 of a breath alcohol measuring device 19. The entire sample collector 1 is made of plastic and therefore is especially hygienic, easy to clean and may preferably be configured as a replaceable disposable part.

A funnel-shaped retaining element 11, which ensures a nozzle-like guide for the breathing gas stream in the main flow duct 10 and further represents a flow obstacle for backflows out of the bottom area of the sample collector 1 in the direction of the sample inlet 2, is fastened to the sample collector 1 by means of suitable fastening elements 14 in the area of the sample inlet 2. It is essential here that the sample inlet 2 and the retaining element 11 are configured such that the breath sample is discharged without the test subject having to touch the sample inlet 2. The breath sample discharged into the sample inlet 2 of the sample collector 1 flows through the retaining element 11, which has a conical or nozzle-like configuration, through the main flow duct 10 in the direction of the collector outlet 3. It is generally conceivable that the sample inlet 2 with the retaining element 11 are configured as one component or as separate components that can be connected to one another by means of fastening elements 14, and this component or these two components is/are connected to the remaining parts of the sample collector 1. It is likewise conceivable to manufacture the sample collector 1 with the sample inlet 2 and with the retaining element 11 as a one-part component, especially from plastic.

The embodiment of the retaining element 11 shown in FIG. 2 makes possible, on the one hand, a reliable feeding of the breath sample into the interior of the sample collector 1 and, in addition, a backflow of at least a part of the breath sample in the direction of the sample inlet 2 is prevented in a reliable manner. This is achieved by the retaining element 11, which has a funnel-shaped configuration, protruding into the main flow duct 10 of the sample collector 1 and covering about half of the cross-sectional surface, so that a dead space zone 18, in which breathing gas is partially collected, is formed on both sides of the funnel-shaped retaining element 11 between the retaining element 11 and the outer wall 12.

It is essential that an outflow opening 6, through which a part of the breath sample discharged into the sample collector 1 leaks into the surrounding area 7, is in turn provided with a plurality of slotted or rectangular openings 23 in the direction of flow of the discharged breath sample behind the retaining element 11. Finally, downstream of this outflow opening 6 is located the collector outlet 3, which has three outlets, wherein a part of the breathing gas streams out via an opening 24 on the bottom side of the collector outlet 3 and is preferably guided into a measured gas duct 21 of a measuring unit 9 (not shown here) of a breath alcohol measuring device 19 for the measurement of the breath alcohol content. In addition, the collector outlet 3 has two lateral outlets 15, at which the main flow duct 10 opens into the surrounding area 7. Via these outlets 15, both the part of the breathing gas sample, which was not used for the breath alcohol measurement, and the part used for the breath alcohol measurement advantageously flow into the surrounding area 7. The main flow duct 10 has a trapezoidal cross section in the area of the collector outlet 3 in the direction toward the outlets 15, wherein the part of the breathing gas sample not guided toward the opening 24 on the bottom side is deflected by about 90° in the direction toward the two lateral outlets within the collector outlet 3.

It is essential for the present invention that the sample collector 1 is configured such that a uniform flow through the main flow duct 10 is guaranteed within the sample collector 1. The outflow opening 6 may generally have one opening or a plurality of openings and may be positioned in the direction of flow in front of, after or in the area of an inlet of a measured gas duct 21, which leads to the sensor 16 of the measuring unit 9. The outflow opening thus establishes a connection between the main flow duct 10 and the surrounding area 7 in addition to the outlet 15 at the end of the main flow duct 10. It is generally likewise conceivable to provide at least two outflow openings 6, which are arranged one behind the other in the direction of flow. In any case, the at least one additional outflow opening 6 is configured such that due to the introduction of a breath sample into the sample inlet 2 of the sample collector 1 and thus into the main flow duct 10, a pressure difference to the surrounding area 7 is built up at the sensor 16 and/or at an additionally provided pressure sensor (not shown) for actuating a pump unit, which supplies the sensor 16 with the necessary breathing air sample, in order to trigger a measurement at the sensor 16.

Furthermore, the outflow opening 6 is configured such that possible environmental effects, as they are caused, for example, by wind or special temperature and/or humidity values or by fluctuations of these values, and which may cause an independent triggering of the sensor, are ruled out. The outflow opening 6 is further arranged such that the part of the breath sample flowing out of the main flow duct 10 through this additional outflow opening 6 is not hindered by a hand of the test subject. A corresponding gripping surface of the breath alcohol measuring device 19, especially in the area of a housing of the measuring unit 9, is hence arranged at a sufficiently spaced location from the outflow opening 6. Because of the provision of the outflow opening 6, the sample collector is flushed better than prior-art mouthpieces, so that not only backflows to the test subject are prevented or at least minimized, but also the accuracy of the breath alcohol measurement is increased.

Figure 3:
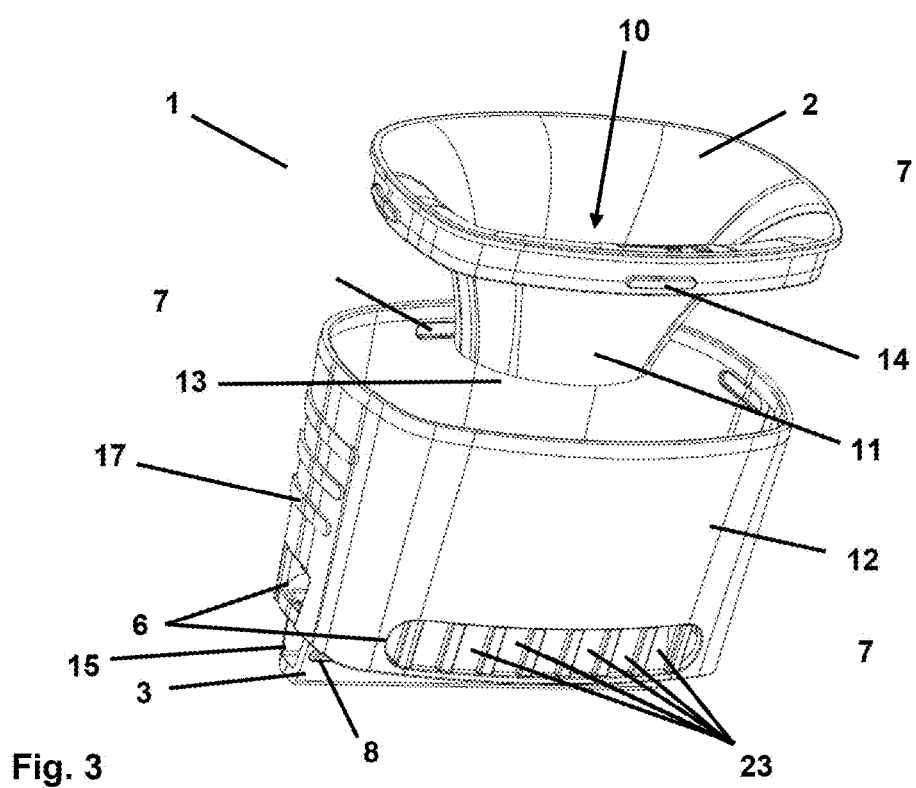
FIG. 3 is a perspective view of a sample collector configured according to the present invention with the sample inlet removed.

FIG. 3 shows in a perspective view the sample collector 1 configured according to the present invention, which has, on the one hand, a housing 22 and, on the other hand, a component, which has a sample inlet 2 and a retaining element 11 and which can be fastened to the housing by means of fastening elements 14. The component in which the sample inlet 2 and the retaining element 11 are integrated and the housing together form the sample collector 1 according to this embodiment.

FIG. 3 shows the housing 22 of the sample collector 1 and the sample inlet 2 as well as the retaining element 11 in a state in which they are separated one from another. In order to fasten the component, which has the sample inlet 2 with the retaining element 11, to the housing 22, this component is inserted into the sample collector 1 and the four snap-in lugs, which are provided as fastening elements 14, snap in corresponding recesses on the inner circumference of the housing 22. In order to remove the component again from the housing 22 of the sample collector 1, the snap-in lugs are again removed from the corresponding recesses, for example, by firm pulling of the component or by at least partial pressing in.

It is, in turn, essential for the sample collector 1 shown in FIG. 3 that an outflow opening 6 be provided with a plurality of rectangular slot openings 23 in the bottom area, through which slot openings 23 the at least one part of the breath sample blown into the sample inlet 2 of the sample collector reaches the surrounding area 7 from the main flow duct 10. The remaining part of the breath sample, which was not discharged through the outflow opening 6 into the surrounding area 7, is guided downstream of the outflow opening 6, on the one hand, to the lower opening 24 of the collector outlet 3, which a measured gas duct 21 adjoins in the operating state, in which the sample collector 1 is connected to a measuring unit 9, and, on the other hand, is deflected and guided to the lateral outlet openings 15. The discharged breathing gas sample reaches the surrounding area 7 through the outlet openings 15 of the collector outlet 3, which outlet openings are arranged in this case on two opposite sides of the collector outlet 3. Within the collector outlet, the main flow duct 10 is thus split at least temporarily into three partial ducts, namely two partial flows, which reach the surrounding area via the lateral outlet openings 15, and one partial flow, which can be introduced into the measured gas duct 21 of a measuring unit 9 via the bottom opening 24.

Elements 17 in the form of small projections, which make possible an easy grasping and fastening of the sample collector at the breath alcohol measuring device for the test subject, are provided on the outer side walls of the sample collector 1, here of the sample collector housing 22.

FIG. 4 shows in two views a breath alcohol measuring device with a sample collector 1 provided for it. FIG. 4a shows the measuring unit 9 of the breath alcohol measuring device with the sample collector 1 fastened to it in a front view. In addition, FIG. 4b shows the measuring unit 9 with the sample collector fastened to it in a sectional view rotated by 90°.

The measuring unit 9 has in the lower area a gripping surface 25 with suitable recesses, which guarantee a secure grasping, holding and handling of the alcohol measuring device. In addition, a power supply 20 with a battery, a central control and analysis unit 4 as well as an output unit 5 in the form of a display are located in the interior of the measuring unit 9. Especially information in relation to the breath alcohol content contained in a tested breath sample are outputted via the output unit 5.

After the sample collector 1 has been fastened to the measuring unit 9 and the device has been put into the operating state, breath samples discharged by test subjects can be tested for their alcohol content. It is essential for the breath alcohol measuring device shown that a test subject is able to discharge a breath sample, without there being contact between the sample collector 1 or its sample inlet 2 and the mouth of the test subject. Rather, the breath sample is only blown into the sample inlet.

The breath sample discharged into the sample inlet 2 of the sample collector 1 flows through the sample collector 1, wherein a part of the breathing gas stream is released into the surrounding area via the outflow opening 6, which has a plurality of slotted openings 23 or housing openings. The part not released flows into the collector outlet 3 and here partly through the lateral outlet openings into the surrounding area 7 or via the opening 24 into the measured gas duct 21, which is located within the measuring unit 9 of the breath alcohol measuring device. The part of the breathing gas sample discharged to be tested reaches the sensor 16 via the measured gas duct 21, which sensor 16 generates a measured signal as a function of the breath alcohol content and sends the measured signal to a central control and analysis unit 4. Based on the measured signal, the control and analysis unit 4 determines a value for the alcohol content of the discharged sample, so that corresponding information can be provided by the output unit 5 which is configured as a display. The breathing gas located in the measured gas duct 21 flows back into the collector outlet 3 after the measurement has been carried out and here via the lateral outlets 15 into the surrounding area 7.

The outflow opening 6 with a plurality of slotted openings 23 in the housing 22 of the sample collector 1 is in turn an essential technical feature for the breath alcohol measuring device shown in FIG. 4. This outflow opening guarantees a good flow through the sample collector 1, which also almost does not vary in case of sample collections carried out at different times.

Figure 5:
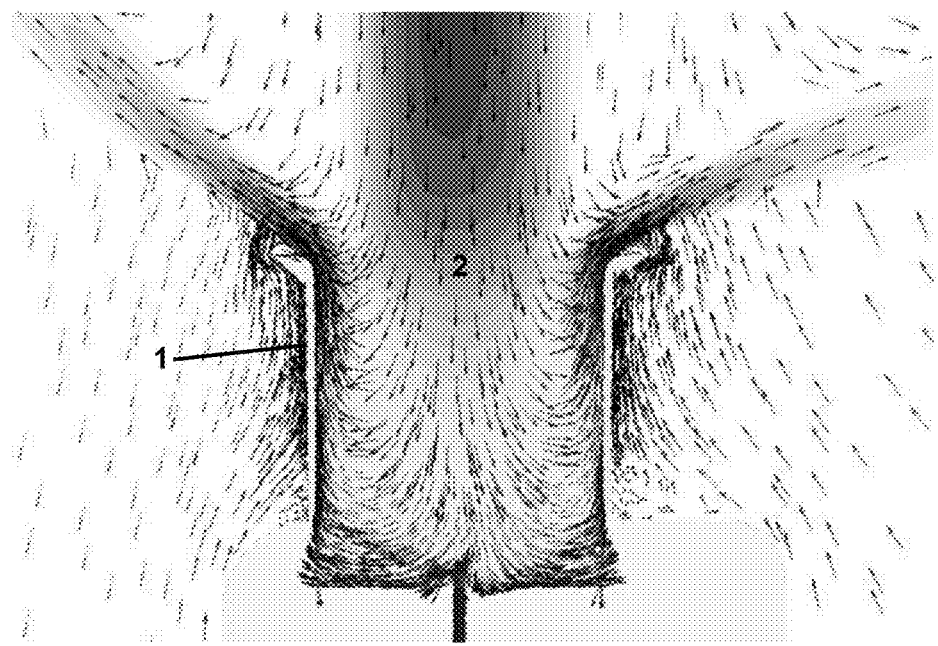
FIG. 5 is a view showing flow graphics of a closed funnel mouthpiece.

The advantage achieved by the present invention, namely an improved flow through the main flow duct 10 and especially through the part of the main flow duct 10 that is arranged within the sample collector 1 is illustrated in FIGS. 5 and 6. In this connection, FIGS. 5 and 6 show the results of flow simulations which have been carried out, on the one hand, at a sample collector 1 that does not provide special outflow openings, and, on the other hand, at a sample collector configured according to the present invention with special outflow opening 6 in the form of a plurality of rectangular slots 23. Both figures show each in a sectional view the sample collector 1, wherein the flow or flow rate of the breath sample discharged by the test subject in the interior of the sample collector 1 is visualized by means of arrows. The arrows represent here the direction of the flow in the respective area, where there is an especially strong flow in areas, in which the flow arrows shown are located especially close to one another, and the flow rate in these areas is especially high.

As was already mentioned in the introduction, FIG. 5 shows the flow through the sample collector, which does not have the outflow opening 6 provided according to the present invention, which outflow opening 6 connects the main flow duct 10 in the interior of the sample collector 1 to the surrounding area 7. The simulation carried out illustrates that both comparatively high dynamic pressures, swirlings or high flow rates occur circumferentially at the sample inlet 2 and in the lower corners of the sample collector 1. Furthermore, it can be seen that the flow reverses at least partly, especially in the area of the sample inlet 2, so that the test subject would feel a backflow of the breath sample in the face. This may lead to falsifications of the measurement result, on the one hand, and this is regularly perceived to be unhygienic by a test subject, on the other hand.

By contrast to a solution without at least one additional outflow opening, FIG. 6 shows a flow pattern of a sample collector 1 configured according to the present invention, which flow pattern was likewise obtained by means of a flow simulation. It is essential here that in the lower area of the sample collector 1 an outflow opening 6 is provided with a plurality of rectangular slots 23, through which at least a part of the breath sample discharged through the sample inlet 2 into the sample collector 1 is released into the surrounding area.

It can be clearly seen, on the one hand, that because of the outflow opening 6 with slots 23 provided according to the present invention, a uniform flow through the sample collector 1, especially in its funnel-shaped area, is achieved. Backflows of the breath sample, which would lead to a flow into the face of the test subject, are almost ruled out. Furthermore, the special configuration of the collector outlet 3, which has, on the one hand, a small central outflow opening 6 and furthermore two openings with trapezoidal cross section provided on both sides of the sample collector 1, provides a deflection of the flow in the main flow duct 10, so that in the upper, funnel-shaped part of the sample collector 1 comparatively large swirls are generated that preferably engulf the breath sample flowing centrally through the sample inlet 2 into the main flow duct 10. Furthermore, the deflection of the flow in the area of the collector outlet 3 leads to a uniform flow and to high flow rates in the area of the lateral outlets 15 of the collector outlet 3, so that a suction is generated here in a suitable manner. A part of the breath sample, which can be fed for a measuring of the breath alcohol content in a measuring unit 9, flows out through the comparatively small opening 24 at the bottom of the collector outlet. The opening 24 is also configured such that because of the comparatively small flow cross section, a high flow rate and thus flow in the area of the opening 24 is achieved.

FIG. 6 thus shows clearly that, on the one hand, backflows or dead space zones within the sample inlet 2, which are especially disadvantageous from a hygienic point of view, are at least almost prevented, and, on the other hand, a uniform flow through the sample collector 1 is ensured.

Due to the at least one additional outflow opening 6 provided according to the present invention, preferably with a plurality of slots 23, a uniform flow through the sample collector 1 is thus made possible and at the same time a suitable supply of the sensor 16 provided for determining the breath alcohol in the measuring unit 9 of a breath alcohol measuring device, which measuring unit 9 is arranged downstream in relation to the flow, is achieved.

While specific embodiments of the invention have been shown and described in detail to illustrate the application of the principles of the invention, it will be understood that the invention may be embodied otherwise without departing from such principles.

The invention claimed is:

1. A device for the measurement of breath alcohol, the device comprising a funnel-shaped sample collector, into which a discharged breath sample can be introduced by the test subject via a sample inlet, and wherein the sample collector comprises a collector outlet;

a measuring unit;

a sensor arranged in the measuring unit, to which at least a part of the breath sample discharged into the sample inlet can be fed and which generates a measured signal based on an alcohol content contained in the breath sample;

a control and analysis unit, which determines the alcohol content of the breath sample based on the measured signal; and an output unit, wherein the control and analysis unit sends a result-specific signal to the output unit, which provides information about the breath alcohol content of the breath sample, wherein the sample collector and the sample inlet are configured as a contactless breath sample introduction means for introducing the breath sample into the device without contacting the device, the contactless breath sample introduction means comprising a measured gas duct, a main flow duct extending in the interior of the sample collector and adjoining the sample inlet, the main flow duct receiving a part of the breath sample discharged into the sample inlet, which part of the breath sample acts at least at times on the sensor via the measured gas duct and which opens into a surrounding area in a direction of flow behind the measured gas duct via an outlet of the main flow duct, and wherein at least one additional outflow opening is provided between the sample inlet and the outlet of the main flow duct, such that a part of the breath sample is introduced into the sample inlet, and then emerges through the at least one outflow opening into the surrounding area; through which at least one additional outflow opening another part of the breath sample introduced into the sample inlet is released into the surrounding area;

wherein the at least one outflow opening is located between the sample inlet and the collector outlet of the sample collector;

wherein the sample collector has at least one funnel-shaped retaining element, which protrudes inwardly into the main flow duct, and which produces a nozzle-like guide for the respiratory gas stream in the main flow duct, and is configured to at least partially impede a backflow of the breath sample in the direction of the sample inlet.

2. A device in accordance with claim 1, wherein a cross section of the main flow duct becomes smaller in at least some sections in the direction of flow of the discharged breath sample.

3. A device in accordance with claim 1, wherein:
the sample collector has a collector outlet, via which the breath sample discharged into the sample collector is introduced into the measuring unit, in which the sensor is arranged, via the collector outlet and the at least one additional outflow opening is located between the sample inlet and the collector outlet.

4. A device in accordance with claim 1, wherein the sample collector has at least one fastening element, by which the sample collector can be connected to the measuring unit, in which the sensor is arranged, wherein the main flow duct extends in the measuring unit and the measured gas duct forms a branch in the measuring unit, via which branch a partial breathing gas stream is fed to the sensor at least at times as a function of a control signal generated by the control and analysis unit.

5. A device in accordance with claim 1, wherein the outflow opening is shaped and dimensioned such that after the breath sample has been introduced into the sample collector, a pressure which is different than the pressure in the surrounding area is generated at the sensor or at a pressure sensor, the measured signal of which is used as the basis for actuating a pump unit to supply the sensor with at least the part of the breath sample.

6. A device in accordance with claim 1, wherein the retaining element is configured in an area of the sample inlet as a partition enclosing the main flow duct and projecting from an inner wall of the sample collector.

7. A device in accordance with claim 1, wherein the retaining element comprises at least one fastening element which is configured to non-destructively connect the retaining element to the sample collector and non-destructively detach the retaining element from the sample collector after the connection.

8. A device in accordance with claim 1, wherein the at least one outflow opening comprises at least two slots made in an outer wall of the sample collector.

9. A device in accordance with claim 1, wherein the at least one outflow opening comprises a plurality of openings, which are made in an outer wall of the sample collector distributed over a circumference of the flow duct.

10. A device in accordance with claim 1, wherein a cross section of the main flow duct decreases from the sample inlet to a collector outlet in the sample collector.

11. A device in accordance with claim 1, wherein an abrupt reduction of the cross section of the main flow duct is provided between the outflow opening and the collector outlet.

12. A device in accordance with claim 1, wherein the main flow duct of the sample collector has a trapezoidal cross-sectional shape in at least one plane in the area of the collector outlet.

13. A device in accordance with claim 1, wherein at least one flow-influencing component, comprising one or more of a screen, a diaphragm, a flap and/or a valve is arranged between the sample inlet and the sensor.

14. A breathing alcohol measurement device comprising: a sample collector comprising a sample inlet for introducing a breath sample, discharged by a test subject into the sample collector, a sample collector outlet to an environment of the device and a main flow duct within the sample collector connecting the sample inlet to the sample collector outlet;

a measuring unit; a sensor arranged in the measuring unit;

a measuring gas duct associated with the measuring unit for feeding a portion of the breath sample introduced into the sample collector to the sensor, which produces a measurement signal on the basis of an alcohol content contained in the breath sample, the measuring gas duct having a fluid communication opening with the main flow duct at a location such that a portion of the breath sample introduced into the sample collector that flows out of the sample collector outlet flows past the fluid communication opening;

a control and evaluation unit configured to determine the alcohol content of the breath sample based on the measurement signal; and an output unit, the control and evaluation unit further being configured to transmit a result-specific signal to a unit output unit, providing information on the breath alcohol content of the breath sample; and an outflow opening arrangement, between the sample inlet and the outlet, through which a further portion of the breath sample introduced into the sample collector flows into the environment of the device;

and wherein the sample collector comprises at least one funnel-shaped retaining element, which protrudes inwards into the main flow duct and which is configured to at least partly prevent a backflow of the breath sample in the direction of the sample inlet.

15. A breathing alcohol measurement device in accordance with claim 14, wherein cross section of the main flow duct becomes smaller in at least some sections in a direction of flow of the discharged breath sample.

16. A breathing alcohol measurement device in accordance with claim 14, further comprising a pumping unit, wherein the control and evaluation unit is configured to actuate the pump unit to feed said portion of the breath sample introduced into the sample collector to the sensor at least at times.

17. A breathing alcohol measurement device in accordance with claim 14, wherein the outflow opening arrangement is shaped and dimensioned such that after the breath sample has been introduced into the sample collector, a pressure which is different than the pressure in the surrounding area prevails and a measured signal is generated at the sensor or at a pressure sensor, and the measured signal is used by the control and evaluation unit as a basis for actuating the pump unit to supply the sensor with said portion of the breath sample.

18. A breathing alcohol measurement device in accordance with claim 14, wherein the outflow opening arrangement comprises a plurality of openings defined by an outer wall of the sample collector and distributed over a circumference of the main flow duct.

* * * * *